United States Patent [19]

Diezel

[11] Patent Number: 5,679,359
[45] Date of Patent: Oct. 21, 1997

[54] WATER-SOLUBLE MAGNESIUM SALTS IN EXTERNALLY APPLICABLE FORMULATIONS AND NEW COMBINATION PREPARATIONS

[75] Inventor: Wolfgang Diezel, Berlin, Germany

[73] Assignee: Wogepharm GmbH, Hurth, Germany

[21] Appl. No.: 530,172

[22] PCT Filed: Mar. 23, 1994

[86] PCT No.: PCT/EP94/00910

§ 371 Date: Jan. 4, 1996

§ 102(e) Date: Jan. 4, 1996

[87] PCT Pub. No.: WO94/22421

PCT Pub. Date: Oct. 13, 1994

[30] Foreign Application Priority Data

Apr. 2, 1993 [DE] Germany .................. 43 10 816.4

[51] Int. Cl.$^6$ ........................................ A01K 7/48
[52] U.S. Cl. .................. 424/401; 424/677; 424/681; 514/844; 514/969
[58] Field of Search .................. 424/401, 677, 424/681; 514/844, 969

[56] References Cited

FOREIGN PATENT DOCUMENTS

| | | |
|---|---|---|
| 0 399 909 | 11/1990 | European Pat. Off. . |
| 0 565 007 | 10/1993 | European Pat. Off. . |
| 883477 | 7/1960 | France . |
| 2 122 613 | 1/1972 | France . |
| 2 697 750 | 11/1992 | France . |
| 33 27 840 | 8/1983 | Germany . |
| 38 00 971 | 1/1988 | Germany . |
| 297 062 | 8/1990 | Germany . |
| 43 15 866 | 5/1993 | Germany . |
| 02011518 | 1/1990 | Japan . |
| 69186 | 7/1960 | Romania . |

*Primary Examiner*—Jyothsan Venkat
*Attorney, Agent, or Firm*—Jacobson, Price, Holman & Stern, PLLC

[57] ABSTRACT

Water-soluble magnesium salts in preparations for an external application are suitable to weaken UV-induced damages to the skin, especially premature aging of the skin and the formation of skin cancer. The effect is enhanced by a combination with vitamin E and/or vitamin E esters.

3 Claims, No Drawings

WATER-SOLUBLE MAGNESIUM SALTS IN EXTERNALLY APPLICABLE FORMULATIONS AND NEW COMBINATION PREPARATIONS

The present invention relates to the use of water-soluble magnesium salts in formulations which are to be externally applied and to the use of water-soluble magnesium salts for the manufacture of external formulations as well as to novel external preparations containing water-soluble magnesium salts in combination with vitamin E and/or vitamin E esters.

From EP-A 0 439 640 there has been known that inflammatory diseases of the skin and allergically inflammatory reactions of the skin can be treated with externally applicable formulations containing from 0.5 to 30% by weight of water-soluble magnesium salts. It is an essential feature of these external preparations that they contain no or virtually no calcium ions, so that calcium can be displaced by magnesium, thereby to inhibit the inflammation enzymes. Such a preparation meanwhile has been marketed by Applicant under the designation of Wogederm®. It contains 25% by weight of magnesium chloride, conventional ointment bases and no added calcium salts.

It has now been determined that such preparations containing at least 0.5% by weight, and preferably 5% by weight, of water-soluble magnesium salts are further capable of lessening UV light-induced damages to the skin and thereby, more particularly, to weaken, or even fully prevent, premature aging and the generation of skin cancer by UV light. It has further been determined that the light-protective action known from DE-A-35 07 791 of vitamin E and/or vitamin E esters is significantly enhanced by the simultaneous presence of water-soluble magnesium salts, so that it offers itself to provide combination preparations which contain a) from 0.5 to 30% by weight of water-soluble magnesium salts and b) from 0.4 to 25% by weight of vitamin E and/or vitamin E ester.

Since the magnesium salts in the externally applicable formulations are to be water-soluble, it is primarily magnesium chloride that is taken into consideration. Magnesium sulfate is less suitable. Also the other water-soluble magnesium salts, including those of organic acids, must be well tolerated and, above all, must not induce any allergic reaction or other irritation of the skin.

The formulations considered for external application mainly include ointments, creams, lotions, aqueous tonics and shampoos. These in the first place are cosmetic preparations, while also preparations are contemplated that can be marketed only as drugs. This will, more specifically, depend on whether the base and auxiliary materials are allowed for the manufacture of cosmetics or solely for the formulation of drugs, and whether the preparations will be offered also for other purposes illustrated by a statement on healing and, hence, are declared as medicaments.

The preparations used according to the invention, depending on the intended use, may be produced as water-in-oil or as oil-in-water emulsions which will either fast penetrate into the skin or will at least partially remain as a greasy film on the surface of the skin for an extended period of time. The water-soluble magnesium salts from lotions, aqueous tonics and shampoos in general will fast penetrate into the skin so that they may display their light-protective action therein. The concentration of magnesium salts, and especially of magnesium chloride, may be selected to be between 0.5% and 30% by weight, depending on the kind of application. It is preferred that concentrations between 5 and 30% by weight are selected.

The contents of vitamin E and/or vitamin E esters may also be selected from within wide limits of between 0.4% and 25% by weight. It is preferred that the compositions contain from 5% to 20% by weight of vitamin E and/or vitamin E ester. Preferred are formulations from which vitamin E and/or vitamin E ester can readily penetrate into the skin, such as those according to DE-B-35 07 791 and to EP-B 0 158 090.

Thus, the new external preparations according to the invention containing the combination of water-soluble magnesium salt and vitamin E and/or vitamin E esters primarily utilize ointment bases which are suitable to facilitate the penetration into the skin of vitamin E and/or its esters. For this reason, formulations based on oleic acid oleyl ester which optionally further contain emulsifiers and/or blood circulation-promoting and vasodilative substances are especially preferred. In these formulation magnesium chloride can be incorporated in sufficient amounts, so that the duplicate effect may be realized.

The UV light-induced damages to the skin, more particularly premature aging and the generation of skin cancer, have been known. They are attributed to an induction of free-radical initiated reactions and/or to the UV light-induced lipid peroxidation {R. Hochschild: Exp. Geront. 6 (1971) 153; H. Meffert et al.: Experientia 32 (1976) 1397; T. Günther: Mag.-Bull. 13 (1991) 78, as well as B. D. Goldstein and G. Witz: Free Rad. Res. Commun. 11 (1990) 3; E. A. Emmelt: CRC Crit. Rev. Toxicol. 2 (1973) 211; F. Urbach: J. Invest. Dermatol. 32 (1959) 373}.

In the course of the lipid peroxidation there are formed fatty acid hydroperoxy radicals and lipoperoxides which to a significant extent will undergo decomposition to form malonic dialdehyde (MDA). Malonic dialdehyde will form Schiff bases with amino groups of the tissue, more specifically with amines, proteins and nucleic acids. These Schiff bases derived from malonic dialdehyde obviously cannot be any more degraded by cell-endogenous enzymes. This is why malonic dialdehyde leads to an increased cross-linking of collagen and, hence, to some premature skin aging. The Schiff bases formed by malonic dialdehyde of nucleic acids (DNA) obviously are to a significant extent responsible for the formation of the UV B light-induced damages to the skin, which may extend from cell damage to cell death or to cell degeneration.

It has now been determined that magnesium ions in a sufficient concentration, alone by themselves or to an enhanced degree in the presence of vitamin E and/or vitamin E esters, inhibit the UV light-induced lipid peroxidation. There has further been detected that the formation of so-called "sunborn cells" attributed to the UV light-induced DNA damage is significantly reduced after magnesium ions have been provided in accordance with the present invention.

The effects produced by magnesium ions and by magnesium ions in combination with vitamin E will be apparent from the results of the following examinations.

EXAMPLE 1

Surgically removed human skin (2 cm×1 cm) were irradiated with UV B light (1.2 J/cm$^2$). Each of the substances specified in the subsequent Table 1 was applied thereonto one hour prior to the irradiation. The amounts applied onto the area of 2 cm×1 cm were 200 μl each. After the irradiation, the epidermis was mechanically separated {E. J. van Scott: J. Invest. Dermatol. 18 (1952) 377}. The recovered epidermis (300 mg) was homogenized with 150 mmol/l of KCl and further worked up {Method: R. S. Britton et al.: Hepatology 11 (1990) 93; T. Günther et al.: Mag.-Bull 14 (1992) 57}. The malonic dialdehyde contents in the epidermis was quantitatively determined. As is evident from the following Table 1, magnesium ions are capable of minimizing the UV light-induced malonic dialdehyde formation. The treatment of the skin with a combination of magnesium ions + vitamin E enhances this effect.

TABLE 1

|  | n[4] | Malonic Dialdehyde (μmol/kg) | <p[5] |
|---|---|---|---|
| Control (No UV B Irradiation) | 10 | 2.075 ± 0.15 |  |
| UV B[1] | 8 | 16.030 ± 2.42 | 0,001 |
| UV B + Vitamin E[2] | 8 | 6.800 ± 1.63 | 0,01 |
| UV B + MgCl$_2$ (100 mM)[3] | 4 | 13.080 ± 3.51 | 0,001 |
| UV B + MgCl$_2$ (500 mM) | 4 | 6.890 ± 1.42 | 0,01 |
| UV B + MgCl$_2$ (1,000 mM) | 4 | 7.961 ± 1.24 | 0,01 |
| UB B + Vitamin E + MgCl$_2$ (500 mM) | 4 | 2.240 ± 0.20 | n.s. |
| UV B + Vitamin E + MgCl$_2$ (1,000 mM) | 4 | 2.800 ± 0.38 | n.s. |

[1] UV B light: 1.2 J/cm$^2$
[2] Vitamin E (α-tocopherol: 0.5%)
[3] MgCl$_2$.6H$_2$O (500 mM = 1%)
[4] Number of examined skin samples
[5] Wilcoxon Test: statistical difference from control:
n.s.: no significant difference

EXAMPLE 2

Reduced generation of UV light-induced "sunborn cells" in human epidermis as a consequence of the pre-treatment of the skin with a cream containing magnesium ions (Wogederm® Magnesium-Creme) (Table 2).

As a consequence of an external treatment with magnesium ions, a lower amount of "sunborn cells" is generated during a light therapy (Table 2). "Sunborn cells" are formed upon a UV light-induced DNA damage, primarily also by a DNA damage due to the UV light-induced lipid peroxidation {K. Danno et al.: Photochem. Photobiol. 45 (1987) 683}. Such UV light-damaged cells may degenerate to form cancer cells.

TABLE 2

|  | n[2] | "Sunborn cells" per 1 mm of Epidermis (x ± s) | p[3] |
|---|---|---|---|
| Ointment Base + UV Light[1] | 4 | 5.71 ± 1.23 |  |
| Magnesium Cream[4] + UV Light | 4 | 3.03 ± 1.07 | 0,05 |

[1] 28 Days of treatment: Total dose of UV: 7.87 J/cm$^2$
[2] n = Number of patients (of histological examination after 28 days of treatment
[3] Statistical significance of the difference (Mann-Whitney Test)
[4] Wogederm ® Magnesium-Creme.

EXAMPLE 3

Reduced occurrence of UV B light-induced erythema after external treatment of the human skin with magnesium ions (Table 3)

As a test, either the ointment base alone or Wogederm® Magnesium-Creme was applied onto a skin area of 2 cm×2 cm of volunteer test persons 30 min prior to an UV B test irradiation (0.83 mW/cm$^2$). Twenty-four hours later the UV B-induced erythema was determined. As is seen from Table 3, as a result of the action of the magnesium ions there is an average erythema lessening by the factor of 3.73 (erythema-protective factor). When the magnesium cream was applied 1 hour prior to the UV B test irradiation, the resultant erythema-protective factor was 4.48 under otherwise the same conditions.

TABLE 3

| Test Person | Minimum Erythema Dose (J/cm$^2$)[2] | | Erythema-Protective Factor |
|---|---|---|---|
| No. 2 | Ointment Base | Magnesium Cream[1] | (ESF) |
| 1 | 0.015 | 0.060 | 4.0 |
| 2 | 0.015 | 0.050 | 3.3 |
| 3 | 0.015 | 0.040 | 2.7 |
| 4 | 0.010 | 0.100 | 10.0 |
| 5 | 0.005 | 0.005 | 1.0 |
| 6 | 0.005 | 0.015 | 3.0 |
| 7 | 0.005 | 0.015 | 3.0 |
| 8 | 0.001 | 0.020 | 20.0 |
| 9 | 0.001 | 0.001 | 1.0 |
| 10 | 0.005 | 0.015 | 3.0 |
| 11 | 0.015 | 0.015 | 1.0 |
| 12 | 0.005 | 0.010 | 2.0 |
| 13 | 0.080 | 0.080 | 1.0 |
| 14 | 0.015 | 0.020 | 1.3 |
| 15 | 0.015 | 0.030 | 2.0 |
| 16 | 0.005 | 0.015 | 3.0 |
| 17 | 0.080 | 0.120 | 1.5 |
| x ± s | 0.017 ± 0.024 | 0.036 ± 0.035 | 3.73 ± 4.85[3] |

[1] Wogederm ® Magnesium-Creme
[2] UV irradiation with 0.83 mW/cm$^2$ and reading after 24 hours
[3] Application of the magnesium cream 30 minutes before UV B light testing.

EXAMPLE 4

The following components were mixed with each other:

| dl-α-Tocopherol | 5.00 g |
| Magnesium chloride | 5.00 g |
| Miglyol | 15.00 g |
| Water | 5.00 g |
| Lanette Ointment Base | 70.00 g |
|  | 100.00 g |

This mixture yields a cream which is readily spreadable on the skin and will very fast penetrate into the skin. It forms a lasting protection against UV light, has a high light-protective factor and cannot be washed off again with water. The action of the components is due to two entirely different mechanisms of action. Correspondingly good results are attainable with formulations wherein the dl-α-tocopherol contents are varied between 3 g and 10 g, and the magnesium chloride contents are likewise varied between 3 g and 10 g, while the water contents may be approximately adjusted to the magnesium chloride contents.

I claim:

1. A method of protecting the skin against UV light-induced damage comprising applying to the skin a dermatologically acceptable formulation containing in an amount of 0.5–30% by weight and vitamin E in an amount of 0.4% to 25% by weight of the formulation, in the absence of calcium salts.

2. A method of making an externally applicable formulation for weakening UV light-induced damage to the skin comprising compounding in an amount of 0.5 to 30% by weight and vitamin E in an amount of 0.4% to 25% by weight of the formulation with a dermatologically suitable base in the absence of calcium salts.

3. An externally applicable formulation for weakening UV light-induced damage to the skin comprising:
   a) 0.5 to 30% by weight of magnesium chloride; and
   b) 0.4 to 25% by weight vitamin E, a in the absence of calcium salts.

* * * * *